US006054610A

United States Patent [19]
Lee et al.

[11] Patent Number: 6,054,610
[45] Date of Patent: Apr. 25, 2000

[54] METHOD AND APPARATUS FOR PREPARING PURIFIED TEREPHTHALIC ACID AND ISOPHTHALIC ACID FROM MIXED XYLENES

[75] Inventors: Fu-Ming Lee; Wiston Lamshing, both of Katy, Tex.; Randi Wright Wytcherley, Belgrade, Mont.

[73] Assignee: HFM International, Inc., Houston, Tex.

[21] Appl. No.: 09/097,930

[22] Filed: Jun. 16, 1998

Related U.S. Application Data

[60] Continuation-in-part of application No. 09/074,251, May 7, 1998, Pat. No. 5,961,935, which is a division of application No. 08/477,898, Jun. 7, 1995, Pat. No. 5,767,311, which is a continuation-in-part of application No. 08/962,030, Oct. 31, 1997, Pat. No. 5,840,968, which is a continuation-in-part of application No. 08/760,890, Dec. 6, 1996, which is a continuation-in-part of application No. 08/477,898, Jun. 7, 1995, Pat. No. 5,767,311.

[51] Int. Cl.$^7$ .................................................. C07C 51/487
[52] U.S. Cl. .......................... 562/487; 562/485; 562/414
[58] Field of Search ...................................... 562/487, 485, 562/409, 414

[56] References Cited

U.S. PATENT DOCUMENTS

| | | | |
|---|---|---|---|
| 2,811,548 | 10/1957 | Ham et al. | 260/525 |
| 2,829,160 | 4/1958 | Stehman et al. | 260/525 |
| 2,833,816 | 5/1958 | Saffer et al. | 260/524 |
| 2,833,817 | 5/1958 | Saffer et al. | 260/524 |
| 2,849,483 | 8/1958 | Ham | 260/516 |
| 2,891,992 | 6/1959 | Raecks et al. | 260/515 |
| 2,905,709 | 9/1959 | Scheak et al. | 260/515 |
| 2,923,736 | 2/1960 | Maclean | 260/525 |
| 2,949,483 | 8/1960 | Ham | 260/516 |
| 3,330,863 | 7/1967 | Read et al. | 260/525 |
| 3,388,156 | 6/1968 | Sakurai et al. | 260/525 |
| 3,431,296 | 3/1969 | Ichikawa et al. | 260/525 |
| 3,465,035 | 9/1969 | Nakaguchi et al. | 260/525 |
| 3,497,552 | 2/1970 | Olsen | 260/525 |
| 3,505,398 | 4/1970 | Baldwin | 260/525 |
| 3,574,727 | 4/1971 | Taylor et al. | 260/525 |
| 3,584,039 | 6/1971 | Meyer | 260/525 |
| 3,766,257 | 10/1973 | Wimer et al. | 260/515 |
| 3,766,258 | 10/1973 | Engelbrecht et al. | 260/515 |
| 3,859,344 | 1/1975 | Shigeyasu et al. | 260/524 |
| 3,862,218 | 1/1975 | Stautzenberger | 260/525 |
| 3,887,613 | 6/1975 | Blay | 260/525 |
| 3,899,530 | 8/1975 | Syoji et al. | 260/525 |
| 3,931,305 | 1/1976 | Fisher | 260/525 |
| 3,953,502 | 4/1976 | Fassell et al. | 260/525 |
| 4,053,506 | 10/1977 | Park et al. | 260/525 |
| 4,081,464 | 3/1978 | Marsh et al. | 260/524 |
| 4,165,337 | 8/1979 | Yoshinaka et al. | 260/544 |
| 4,197,412 | 4/1980 | Kimura et al. | 562/416 |
| 4,201,871 | 5/1980 | Tanouchi et al. | 562/486 |
| 4,201,872 | 5/1980 | Kimura et al. | 562/487 |
| 4,228,299 | 10/1980 | Ferguson et al. | 560/124 |
| 4,230,882 | 10/1980 | Seko et al. | 561/416 |
| 4,245,078 | 1/1981 | Suzuki et al. | 562/412 |
| 4,260,817 | 4/1981 | Thompson et al. | 562/487 |
| 4,263,452 | 4/1981 | Komatsu et al. | 562/487 |
| 4,268,690 | 5/1981 | Komatsu et al. | 562/416 |
| 4,275,230 | 6/1981 | Donaldson | 562/486 |
| 4,281,179 | 7/1981 | Komatsu et al. | 562/416 |
| 4,286,101 | 8/1981 | Hashizume et al. | 562/487 |
| 4,297,507 | 10/1981 | Komatsu et al. | 562/416 |
| 4,314,073 | 2/1982 | Crooks | 562/416 |
| 4,317,923 | 3/1982 | Imai | 562/487 |
| 4,331,824 | 5/1982 | Ikeda et al. | 585/638 |
| 4,334,090 | 6/1982 | Donaldson | 562/480 |
| 4,340,752 | 7/1982 | List et al. | 562/485 |

(List continued on next page.)

FOREIGN PATENT DOCUMENTS

| | | |
|---|---|---|
| 611607 | 6/1962 | Belgium . |
| 614720 | 9/1962 | Belgium . |
| 615996 | 10/1962 | Belgium . |
| 732838 | 10/1969 | Belgium . |
| 1316914 | 2/1963 | France . |
| 1117100 | 11/1961 | Germany . |
| 818211 | 8/1959 | United Kingdom . |
| 881460 | 3/1960 | United Kingdom . |
| 908011 | 10/1962 | United Kingdom . |
| 1049720 | 11/1966 | United Kingdom . |
| 1290981 | 9/1972 | United Kingdom . |

OTHER PUBLICATIONS

Tr. Vses. Nauch.–Issled. Proekt. Inst. Monomerov (1970), 2(2), 26–32; From:Ref. Zh., Khim. 1971, Abstr. No. 1N166; V.N. Kulakov, et al.; "Purification of Aromatic Dicarboxylic Acids Obtained by Liquid–Phase Oxidation of Dialkyl Derivatives of Aromatic Hydrocarbons".

Abstract—Database WPI XP–002063355, Section Ch, Derwent Publications Ltd., London, GB; Class A41, Appl. No. 96–017160, Pat. No. JP7291896; Mitsubishi Gas Chem. Co., Inc., "Preparation of High–Purity Terephthalic Acid" (Nov. 1995).

Abstract—Database WPI XP–002063356, Section Ch, Derwent Publications Ltd., London, GB; Class A41, Appl. No. 72–77189T, Pat. No. JP47046663B; Toray Ind., Inc., "Crystallization Process for Purification of Materials Containing Trace Impurities" (1969).

*Primary Examiner*—Gary Geist
*Assistant Examiner*—Sreeni Padmanabhan
*Attorney, Agent, or Firm*—Jenkens & Gilchrist, P.C.

[57] ABSTRACT

A method and apparatus for preparing purified terephthalic acid and, optionally, isophthalic acid from mixed xylenes. The method of the present invention purifies the oxidation reactor effluent containing a mixture of terephthalic acid and isophthalic acid as well as minor amounts of 4-carboxybenzaldehyde (4-CBA), 3-carboxybenzaldehyde (3-CBA), and toluic acid isomers, to produce purified terephthalic acid and, optionally, purified isophthalic acid in an integrated process.

22 Claims, 2 Drawing Sheets

U.S. PATENT DOCUMENTS

| | | | |
|---|---|---|---|
| 4,345,089 | 8/1982 | Nagura et al. | 560/77 |
| 4,357,475 | 11/1982 | Hanotier et al. | 562/414 |
| 4,380,662 | 4/1983 | Hanotier et al. | 562/486 |
| 4,415,479 | 11/1983 | Puskas et al. | 502/85 |
| 4,438,279 | 3/1984 | Packer et al. | 562/416 |
| 4,447,646 | 5/1984 | Johnson et al. | 562/487 |
| 4,459,418 | 7/1984 | Greenshields | 549/370 |
| 4,467,110 | 8/1984 | Puskas et al. | 562/487 |
| 4,467,111 | 8/1984 | Puskas et al. | 562/487 |
| 4,485,244 | 11/1984 | Fox et al. | 549/245 |
| 4,490,554 | 12/1984 | Tanaka et al. | 562/486 |
| 4,500,732 | 2/1985 | Petty-Weeks et al. | 562/486 |
| 4,537,980 | 8/1985 | Greenshields | 549/370 |
| 4,540,493 | 9/1985 | Dickerson et al. | 210/669 |
| 4,605,763 | 8/1986 | Kiefer et al. | 562/487 |
| 4,625,059 | 11/1986 | Shibano et al. | 562/600 |
| 4,626,598 | 12/1986 | Packer et al. | 562/487 |
| 4,629,715 | 12/1986 | Schroeder | 502/185 |
| 4,652,674 | 3/1987 | James et al. | 562/414 |
| 4,675,108 | 6/1987 | Dickerson et al. | 210/275 |
| 4,675,438 | 6/1987 | Schwartz et al. | 562/416 |
| 4,728,630 | 3/1988 | Schroeder et al. | 502/185 |
| 4,772,748 | 9/1988 | Hashizume et al. | 562/413 |
| 4,782,181 | 11/1988 | James | 562/487 |
| 4,791,226 | 12/1988 | Puskas et al. | 562/487 |
| 4,808,751 | 2/1989 | Schroeder et al. | 562/487 |
| 4,827,026 | 5/1989 | Brugge et al. | 562/416 |
| 4,833,269 | 5/1989 | Schroeder | 562/484 |
| 4,877,900 | 10/1989 | Tamaru et al. | 562/413 |
| 4,886,901 | 12/1989 | Holzhauer et al. | 560/77 |
| 4,892,972 | 1/1990 | Schroeder et al. | 562/487 |
| 4,933,491 | 6/1990 | Albertins et al. | 562/416 |
| 4,933,492 | 6/1990 | Schroeder et al. | 562/487 |
| 4,937,378 | 6/1990 | Schroeder | 562/487 |
| 4,939,297 | 7/1990 | Browder et al. | 562/485 |
| 4,948,921 | 8/1990 | Green et al. | 562/413 |
| 5,068,410 | 11/1991 | Tanaka et al. | 562/483 |
| 5,095,144 | 3/1992 | Sato et al. | 562/481 |
| 5,095,145 | 3/1992 | Rosen | 562/483 |
| 5,095,146 | 3/1992 | Zeitlin et al. | 562/486 |
| 5,097,066 | 3/1992 | Holzhauer et al. | 562/487 |
| 5,107,020 | 4/1992 | Reeve | 562/416 |
| 5,110,984 | 5/1992 | Janulis | 562/487 |
| 5,113,015 | 5/1992 | Palmer et al. | 562/608 |
| 5,132,450 | 7/1992 | Tanaka et al. | 562/414 |
| 5,159,109 | 10/1992 | Rosen et al. | 562/509 |
| 5,166,420 | 11/1992 | Shiraki et al. | 562/487 |
| 5,169,977 | 12/1992 | Tanaka et al. | 560/78 |
| 5,175,352 | 12/1992 | Iwane et al. | 562/417 |
| 5,175,355 | 12/1992 | Streich et al. | 562/485 |
| 5,183,933 | 2/1993 | Harper et al. | 562/414 |
| 5,189,209 | 2/1993 | Ohta et al. | 562/414 |
| 5,200,557 | 4/1993 | Gee et al. | 562/486 |
| 5,254,719 | 10/1993 | Holzhauer et al. | 560/78 |
| 5,256,817 | 10/1993 | Sikkenga et al. | 562/487 |
| 5,292,934 | 3/1994 | Sikkenga et al. | 562/413 |
| 5,304,676 | 4/1994 | Hindmarsh et al. | 562/414 |
| 5,306,845 | 4/1994 | Yokohama et al. | 568/484 |
| 5,344,969 | 9/1994 | Iwane et al. | 562/486 |
| 5,354,898 | 10/1994 | Schroeder | 562/485 |
| 5,362,908 | 11/1994 | Schroeder et al. | 562/487 |
| 5,563,293 | 10/1996 | Hindmarsh et al. | 562/414 |
| 5,567,842 | 10/1996 | Izumisawa et al. | 562/486 |

METHOD AND APPARATUS FOR PREPARING PURIFIED TEREPHTHALIC ACID AND ISOPHTHALIC ACID FROM MIXED XYLENES

RELATED APPLICATIONS

This application is a continuation-in-part of application Ser. No. 09/074,251, filed May 7, 1998, entitled Method and Apparatus for Preparing Purified Terephthalic Acid, which is a divisional of Ser. No. 08/477,898, filed Jun. 7, 1995, entitled Method and Apparatus for Preparing Purified Terephthalic Acid, now U.S. Pat. No. 5,767,311, and is also a continuation-in-part of application Ser. No. 08/962,030, filed Oct. 31, 1997, entitled Method and Apparatus for Preparing Purified Terephthalic Acid, which is a continuation-in-part of application Ser. No. 08/760,890, filed Dec. 6, 1996, entitled Method and Apparatus for Preparing Purified Terephthalic Acid, which is in turn a continuation-in-part of application Ser. No. 08/477,898, filed Jun. 7, 1995, entitled Method and Apparatus for Preparing Purified Terephthalic Acid, now U.S. Pat. No. 5,767, 311, all four of which are assigned to the same assignee as this application, and the totality of the disclosures of which are hereby incorporated herein by reference for all purposes.

INTRODUCTION

The present invention relates to the production of terephthalic and isophthalic acids and, more specifically, to a method and apparatus for preparing purified terephthalic acid and isophthalic acid from mixed xylenes.

BACKGROUND

Conventional terephthalic acid (TPA) manufacturing processes require relatively high p-xylene purity (99.7+%) in order to improve the quality of the product and reduce the costs of manufacturing. This is due to the fact that such prior art processes use hydrogenation as the main method for purifying the crude terephthalic acid produced in the oxidation section of said processes. Although the hydrogenation method is very selective to eliminate the major impurity, 4-carboxybenzaldehyde (4-CBA) by converting it to p-toluic acid, the method only operates in the presence of a very small amount of 4-CBA (preferably less than 3,000 ppm). Also, the conventional TPA manufacturing processes are not capable of separating TPA from its isomers, such as isophthalic acid (IPA) and phthalic acid (PA).

SUMMARY OF INVENTION

In contrast to the prior art TPA processes described above, the present invention provides a method and apparatus for preparing purified terephthalic acid and, optionally, isophthalic acid from mixed xylenes. Importantly, it can purify the oxidation reactor effluent containing the mixture of terephthalic acid and isophthalic acid as well as minor amounts of 4-carboxybenzaldehyde (4-CBA), 3-carboxybenzaldehyde (3-CBA), and toluic acid isomers, to produce a purified terephthalic acid and, optionally, purified isophthalic acid in an integrated process. These products are useful for the production of fibers, films, plastic bottles, and polyester resin structures, often reinforced by other materials such as glass fiber.

In accordance with the present invention there is provided a method and apparatus for producing purified terephthalic acid and, optionally, purified isophthalic acid from mixed xylenes in an integrated process. In one embodiment, the method of the present invention includes the production of crude mixed acids (including terephthalic acid and isophthalic acid) by the oxidation of the mixed xylenes containing mainly p-xylene and smaller portions of m-xylene and other isomers. The oxidation step produces not only terephthalic acid and isophthalic acid, but also, by incomplete oxidation, 4-CBA, 3-CBA, p-toluic acid, m-toluic acid and other trace amounts of acid and aldehyde isomers. The product resulting from the oxidation step is a liquid dispersion containing unreacted starting materials, solvents, if any have been used, the products of side reactions, particularly those just mentioned, and other materials which are not desired in the sought-for purified terephthalic acid and purified isophthalic acid.

The reactor effluent is fed to a series of crystallizers which allow the solids to grow by evaporating the reaction solvent, preferably acetic acid, through pressure reductions. The slurry from the last crystallizer is filtered and washed. The filtered crystals are then dried to remove the solvent to a level of less than 0.25% in the resulting crude mixed acid crystals. The mother liquor from the filtration is fed to the solvent dehydration unit to recover the solvent (acetic acid) from water for recycling to the oxidizer.

In further accordance with the invention, the crude mixed acids from the dryer of the oxidation section are re-dissolved in a selective crystallization solvent and then terephthalic acid (TPA) is crystallized out of the selective crystallization solvent in one or, preferably, two crystallization stages. Provision is made to separate out the crystallized and progressively purified TPA from the solvent (with or without co-solvents) of the invention. The filter cake of purified TPA ultimately obtained is washed and soaked with water to remove color and the final trace of the selective crystallization solvent from the TPA product.

In order to recover isophthalic acid (IPA) from the crystallizer mother liquor (after TPA solids are removed by filtration), an anti-solvent is added to cause the substantially complete precipitation of TPA from the mother liquor. The substantially TPA-free mother liquor is concentrated, by evaporating the selective crystallization solvent and the anti-solvent, from the mother liquor, and cooled to cause the crystallization of crude IPA. The crude IPA is then further purified by recrystallizing in another selective crystallization solvent.

The invention also contemplates steps to reclaim and recycle the solvents of the invention at each stage of crystallization and washing, and final soaking. Steps are also taken to closely control the delivery of any objectionable materials to the environment.

One important aspect of the present invention is the discovery of solvents which are effective to bring about the purification of TPA as well as IPA from a crude mixture containing TPA, up to 20% IPA, smaller quantities of 3-CBA, 4-CBA, m-toluic acid, p-toluic acid, and others, through crystallization and separation steps. These discoveries may be summarized as follows.

For TPA purification, the selective crystallization solvents useful in the practice of the present invention include those in which (a) the impurities (including IPA) desired to be separated from TPA are relatively more soluble in the solvent than is TPA at substantially every temperature within the desired range of temperatures at which the solvent containing TPA is to be handled, and (b) TPA is more soluble at an elevated temperature and less soluble at a lower or reduced temperature. It is to be understood that the term "selective crystallization solvent" is intended to include any solvents useful in the selective crystallization of TPA as described above.

For IPA purification, the anti-solvent which is to be added to the mother liquor (from TPA crystallization effluent) should cause substantially total precipitation (or crystallization) of TPA from the mother liquor and yet retain the major portion of IPA in the mother liquor. The substantially TPA-free mother liquor is concentrated by evaporation (or distillation) to crystallize crude IPA, which is then separated by filtration and redissolved in a second selective crystallization to yield the purified IPA.

In accordance with the invention, the primary preferred selective crystallization solvent for purifying TPA is N-methyl pyrrolidone (NMP), for the several reasons discussed below, and for its superior performance. It is non-aqueous, thermally stable, non-toxic (environmentally safe), non-corrosive, and commercially available. TPA can be dissolved in NMP at elevated temperatures, and precipitated or crystallized from NMP at lower temperatures. The major impurities such as 4-CBA, 3-CBA, p-toluic acid, m-toluic acid, as well as IPA, have relatively higher solubility in NMP than TPA at all temperatures. Therefore, by lowering the temperature, only TPA tends to crystallize or precipitate from the solution to form purified TPA crystals.

Although NMP is the most preferred selective crystallization solvent, it is to be understood that, in accordance with the present invention, other preferred selective crystallization solvents for purification of crude TPA can be selected from various polar organic solvents including, but not intended to be limited to, N,N-dimethyl acetamide, N,N-dimethyl formarnide, N-formyl piperidine, N-alkyl-2-pyrrolidone (such as N-ethyl pyrrolidone), N-mercaptoalkyl-2-pyrrolidone (such as N-mercaptoethyl-2-pyrrolidone), N-alkyl-2-thiopyrrolidone (such as N-methyl-2-thiopyrrolidone), N-hydroxyalkyl-2-pyrrolidone (such as N-hydroxyethyl-2-pyrrolidone), the morpholines (such as morpholine, and N-formyl morpholine), the carbitols, $C_1$ to $C_{12}$ alcohols, the ethers, the amines, the amides, and the esters, and mixtures thereof.

The primary preferred anti-solvent is methanol, although the anti-solvent for substantially total TPA precipitation from the mother liquor can also be selected from various polar organic solvents including, but not intended to be limited to, methyl ethyl ketone, acetone, $C_1$ to $C_{12}$ alcohols, the carbitols, the esters, the ethers, $C_1$ to $C_{12}$ carboxylic acids, water, and mixtures thereof.

The primary preferred selective crystallization solvent for IPA purification is methanol, although the solvent can also be selected from the group, but not limited to, methyl ethyl ketone, acetone, $C_1$ to $C_{12}$ alcohols, the carbitols, the esters, ethers, $C_1$ to $C_{12}$ carboxylic acids, water, and mixtures thereof.

In order to remove the residual solvent (e.g., NMP) trapped in the crystals of the final TPA product, the washed TPA crystals are preferably fed to a high temperature soaker where water is used to partially or completely dissolve the TPA crystals. The residual solvent (methanol) trapped in the crystals of the final IPA can be removed by drying to the level of less than 0.25%.

In one embodiment, the method of the present invention for purifying crude terephthalic acid (TPA) from a liquid dispersion produced from the oxidation of mixed xylenes comprises the steps of: (a) dissolving the crude TPA in a selective crystallization solvent at a temperature of from about 50° C. to about 250° C. to form a solution; (b) crystallizing purified acid from said solution by reducing the temperature and/or pressure thereof; (c) separating said crystallized purified TPA from said solution; (d) redissolving said separated purified TPA in a selective crystallization solvent to form a second solution; (e) crystallizing second stage purified TPA from said second solution by reducing the temperature and pressure sufficient to flash evaporate solvent from said TPA of said second solution but without cooling said solution below 50° C.; (f) separating said second stage purified TPA from said second solution; (g) washing said separated second stage purified TPA with water; (h) soaking said washed separated second stage purified TPA with water at a temperature between about 150° C. and about 300° C.; (i) filtering and drying said water soaked second stage purified TPA; (j) adding an anti-solvent to said filtered solution in (c) to cause the precipitation of substantially all the TPA; (k) separating said precipitated TPA from said solution in step (j) and combining said precipitated TPA with said the original crude TPA for processing in step (a); (l) evaporating the solvents from said filtered TPA-free solution in step (k) to cause the crystallization of IPA at a temperature from about 5° C. and about 100° C.; (m) separating said crystallized crude IPA from said solution in step (l); (n) redissolving crude IPA in a selective crystallization solvent at a temperature from about 50 to 250° C. to form a second solution; (o) crystallizing purified IPA from said second solution in step (n) by reducing the temperature and pressure sufficient to flash evaporate solvent from said IPA of said second solution but without cooling said solution below about 50° C.; and (p) separating and drying said second stage purified IPA from said second solution.

In this embodiment, the dispersion contains at least 0 to 20% isophthalic acid (IPA), and minor amounts of 4-carboxyaldehyde (4-CBA), 3-carboxyaldehyde (3-CBA) and impurities selected from unreacted starting materials, solvents, products of side reactions and/or other undesired materials. The selective crystallization solvent for TPA purification is selected from the group consisting of N-methyl pyrrolidone, (NMP), N,N-dimethyl acetamide, N,N-dimethyl formamide, N-formyl piperidine, N-alkyl-2-pyrrolidone (such as N-ethyl pyrrolidone), N-mercaptoalkyl-2-pyrrolidone (such as N-mercaptoethyl-2-pyrrolidone), N-alkyl-2-thiopyrrolidone (such as N-methyl-2-thiopyrrolidone), N-hydroxyalkyl-2-pyrrolidone (such as N-hydroxyethyl-2-pyrrolidone), the morpholines (such as morpholine, and N-formyl morpholine), the carbitols, $C_1$ to $C_{12}$ alcohols, the ethers, the amines, the amides, and the esters, and mixtures thereof. The selective crystallization solvent for TPA purification in this embodiment is N-methyl pyrrolidone or N,N-dimethyl acetamide or N-methyl pyrrolidone. The anti-solvent for TPA precipitation from TPA/IPA solution is selected from the group consisting of methanol, water, methyl ethyl ketone, acetone, $C_1$ to $C_{12}$ alcohols, the carbitols, the esters, the ethers, $C_1$ to $C_{12}$ carboxylic acids, water, and mixtures thereof. The selective crystallization solvent for re-crystallization of IPA is selected from the group of methanol, water, methyl ethyl ketone, acetone, $C_1$ to $C_{12}$ alcohols, the carbitols, the esters, ethers, $C_1$ to $C_{12}$ carboxylic acids, water, and mixtures thereof. The anti-solvent is preferably at the antisolvent/solution ratio of 0.1 to 10, and more preferably at a ratio of between 0.5 to 3, to cause the precipitation of TPA.

In another embodiment, the dispersion contains at least 0 to 20% isophthalic acid (IPA) and minor amounts of 4-carboxyaldehyde (4-CBA), 3-carboxyaldehyde (3-CBA), and impurities selected from unreacted starting materials, solvents, products of side reactions and/or other undesired materials. The selective crystallization solvent for TPA purification is selected from the group consisting of N-methyl pyrrolidone (NMP), N,N-dimethyl acetamide, N,N-dimethyl formamide, N-formyl piperidine, N-alkyl-2-pyrrolidone (such as N-ethyl pyrrolidone), N-mercaptoalkyl-2-pyrrolidone (such as N-mercaptoethyl-2-pyrrolidone), N-alkyl-2-thiopyrrolidone (such as N-methyl-2-thiopyrrolidone), N-hydroxyalkyl-2-pyrrolidone (such as N-hydroxyethyl-2-pyrrolidone), the morpholines (such as morpholine, and N-formyl morpholine), the carbitols, $C_1$ to $C_{12}$ alcohols, the ethers, the amines, the amides, and the esters, and mixtures thereof. The selective crystallization solvent for TPA purification is N-methyl pyrrolidone or N,N-dimethyl acetamide.

The following examples illustrate the effectiveness of the selective crystallization solvent in separating TPA and IPA, which is the principle and feature of this invention:

EXAMPLE 1

This example describes the experimental data on the solubility of TPA as well as IPA in NMP as the selective crystallization solvent at three different temperatures under atmospheric pressure. The experiments were conducted in a laboratory flask which was immersed in a constant temperature bath kept at a pre-determined temperature. The liquid phase temperature in the flask was measured by a thermometer. For high temperature measurement, a total reflux condenser was used to recover the solvent losses due to evaporation. During an experimental run, a small incremental quantity of solids was added to the constantly stirred solvent in the flask until no more solids were dissolved and the solution was then considered saturated with the solids at that temperature. The solubility was calculated based on the weight of solvent and the total weight of solids added. Table 1 summarizes the solubility of TPA and IPA in NMP at 15, 40, 70, and 160° C.

TABLE 1

| | | Solubility (gm of solids/100 gm of solvent) | | | |
|---|---|---|---|---|---|
| Solid | Solvent | 15° C. | 40° C. | 70° C. | 160° C. |
| TPA | NMP | 2.8 | 8.0 | 14.0 | 23.0 |
| IPA | NMP | 10.7 | 22.2 | 46.0 | 62.0 |
| 4-CBA | NMP | 18.9** | 27.4 | 66.0 | 125.0* |

*At 110° C.
**At 23° C.

Based on the solubility data shown in Table 1, it is illustrated that TPA can be purified from the mixture of TPA, IPA, and 4-CBA (3-CBA) by crystallization, since both IPA and CBAs tend to remain in the mother liquor due to their higher solubility. The TPA crystals yielded from the mother liquor should have a substantially higher portion of TPA relative to other components than those contained in the mother liquor.

EXAMPLE 2

A solid mixture containing approximately 95 wt % TPA and 5 wt % IPA was added to NMP according to the solubility of TPA in NMP at 160° C. The mixture was then transferred to a cooling crystallizer equipped with a specially designed mixer in order to minimize the crystal breakage, a heating jacket, and a vapor condenser. The crystallizer was slowly heated up to 160° C. and maintained at this temperature for one hour to ensure all the solids were dissolved. The crystallizer was then cooled down to 45° C. in 90 minutes to allow the TPA crystals to grow. The crystallizer content was transferred to a jacketed filter and filtered quickly while maintaining the temperature at 40 to 45° C. An appropriate amount of warm solvent (at 50 to 70° C.) was used to wash the cake. In some cases, a hot water wash of the cake at 95° C. was carried out after a warm solvent wash. The washed cake was dried and analyzed by gas chromatography to determine the product composition. Table 2 sets forth a summary of the results.

TABLE 2

| Run Number | Filter Temp (° C.) | IPA in Feed | IPA in product | Rinse Condition |
|---|---|---|---|---|
| 1A | 41 | 4.94 wt % | 0.21 wt % | 3 times solvent used at 50° C. |
| 2A | 41 | 5.02 wt % | 0.16 wt % | 3 times solvent used at 70° C. |
| 3A | 41 | 5.00 wt % | 0.18 wt % | 3 times solvent used at 53° C. |
| 1B | 41 | 4.94 wt % | 0.15 wt % | same as 1A plus 10 times water at 95° C. |
| 2B | 41 | 5.02 wt % | 0.13 wt % | same as 2A plus 10 times water |
| 3B | 41 | 5.00 wt % | 0.15 wt % | same as 3B plus 10 times water at 95° C. |

The data in Table 2 above demonstrates that the IPA content in TPA was surprisingly reduced (23 to 39 times) depending upon the rinse condition. When the TPA cake from crystallization was rinsed with solvent at 70° C. followed by a water rinse at 95° C. (Run 2B), the IPA content was indeed reduced 39 times by a single-stage crystallization. Following the same procedure, IPA content in TPA mixture can be reduced from 5 wt % to 33 parts per million by weight (ppmw) through a two-stage crystallization.

EXAMPLE 3

This example gives the experimental data on the solubility of TPA as well as IPA in methanol as the selective crystallization at various temperatures under atmospheric pressure. The experimental apparatus and procedures are the same as those set forth for Example 1 above, with the exception that the vapor pressure is greater than atmospheric. The solubility was calculated based on the weight of solvent and the total weight of solids added. Table 3 summarizes the solubility of PTA and IPA in methanol at various temperatures.

TABLE 3

| | Solubility (gm of solid/100 gm of methanol) | |
|---|---|---|
| Temperature (° C.) | TPA | IPA |
| 10 | | 0.03 |
| 25 | 0.09 | 1.82 |
| 50 | 0.47 | 4.00 |
| 160 | | 2.90 |
| 161 | | 15.00 |

It is observed from Table 3 that the solubility of IPA in methanol is roughly 8 to 20 times higher than that of TPA at the temperature ranging from 25 to 50° C. The solubility of TPA in methanol becomes significant only at higher temperatures, such as 160 to 200° C. under pressure.

EXAMPLE 4

From Example 3, it was found that the solubility of IPA in methanol is substantially higher than that of TPA at room temperature (25° C. to 50° C.). Accordingly, experiments were conducted to determine whether the precipitation of TPA from the solution of TPA, IPA and a minor amount of 4-CBA could be effectuated by adding the proper amount of methanol to the solution. This solution can be the mother liquor from the TPA crystallizer after the TPA crystals are removed with a filter. The mother liquor may have the following composition: 100 grams of NMP, 20 grams of TPA, 10 grams of IPA, and a minor amount of 4-CBA (and 3-CBA).

This example shows that adding methanol to the mother liquor can cause essentially total precipitation of TPA, but only minor precipitation of IPA. To a mixture of 100 grams of NMP, 4 grams of TPA, and 1.5 grams of IPA, approximately 210 grams of methanol was added to the room temperature mixture. The total mixture was stirred for about 90 minutes to allow the solids to crystallize and precipitate from the mixture. The crystals were filtered, washed and dried for analysis. It was found that 47.5% of TPA in the mother liquor was recovered, and the crystals contained roughly 99.0 wt % TPA and 1.0 wt % IPA.

To increase the recovery of TPA, the mother liquor was concentrated by removing a part of NMP and the mixture contained 100 grams of NMP, 20 grams of TPA and 10 grams of IPA. Approximately 260 grams of methanol was added to the mixture to cause TPA to crystallize from the mixture at room temperature. Upon the addition of methanol, the mixture was stirred for 90 minutes before filtering the TPA crystals from the slurry. It was found up to 97.5% TPA was recovered from the mother liquor, and the TPA crystals contained 97.3 wt % TPA and 2.7 wt % IPA. The data indicates that 100% TPA recovery can be achieved by removing more NMP from the mother liquor (higher concentration), or by adding more methanol to the mother liquor, or the combination of both.

In a typical mother liquor, the 4-CBA content should be around 0.01 grams per 100 grams of NMP (0.01%). Since the amount of 4-CBA in the mother liquor is very small and the solubility of 4-CBA in NMP is very high around room temperature (shown in Table 1), the addition of methanol should not cause the precipitation of 4-CBA from the mother liquor.

After 100% of TPA from the mother liquor is recovered and recycled by adding methanol, the TPA-free mother liquor can be further processed to recover IPA. Details of the process scheme is presented in FIG. 1 and is described later in the next section.

DESCRIPTION OF THE PREFERRED EMBODIMENTS

Figure 1:
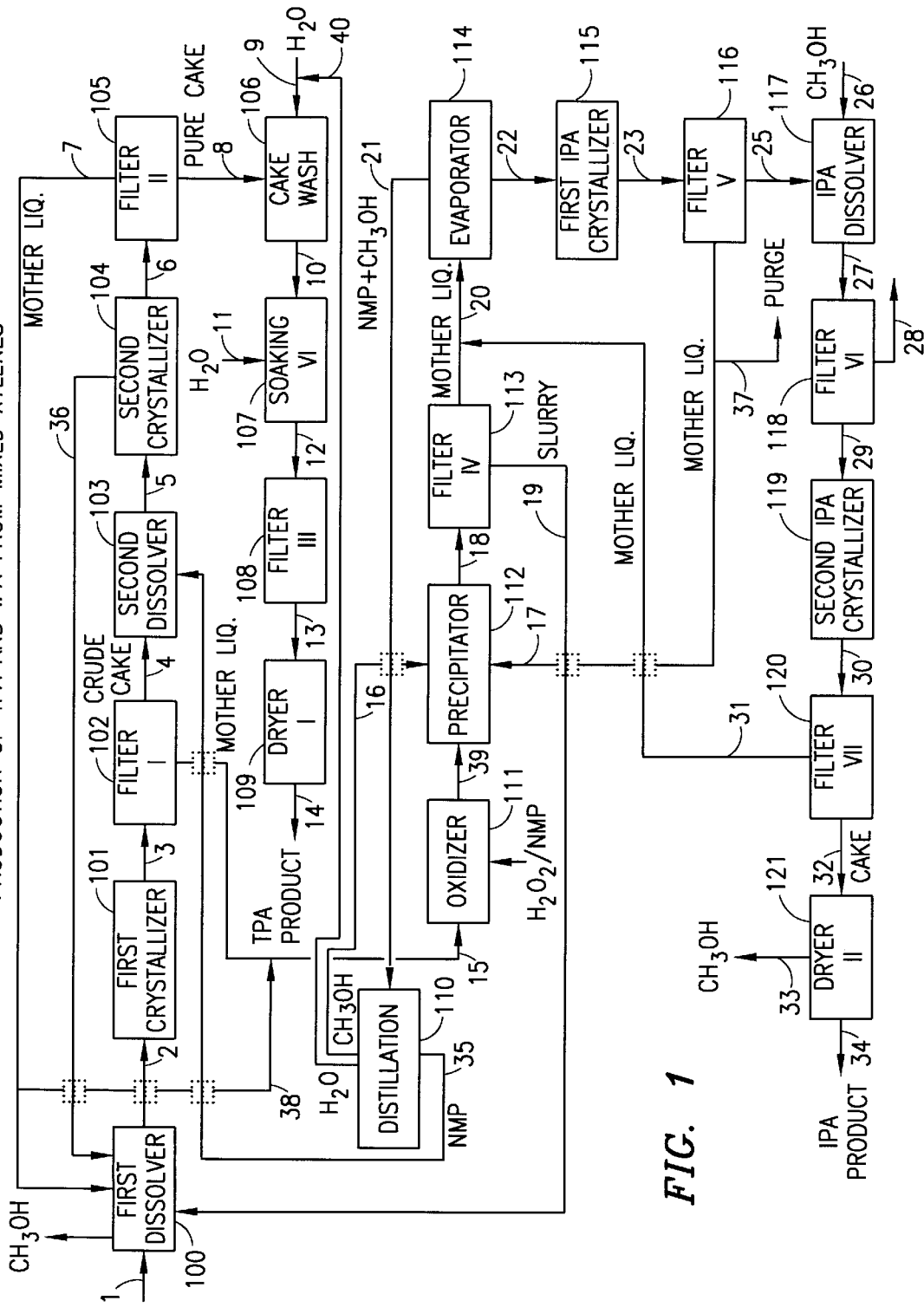
FIG. 1 is a diagrammatic flow chart for a plant for practicing a preferred embodiment of the invention for producing both TPA and IPA.

One of the preferred embodiments of this invention for producing both purified TPA and IPA is presented in FIG. 1.

Now referring to FIG. 1, crude TPA from the oxidation section of a reactor (not shown) containing approximately 95% TPA, 5% IPA, and minor amounts of other impurities (4-CBA, 3-CBA, p-toluic acid, m-toluic acid, etc.), is fed to the First Dissolver 100 through Line 1 to mix with the mother liquor from Filter II 105 (through Line 7) and the slurry from Filter IV 113 (through Line 19). The temperature in the First Dissolver 100 is maintained at 160 to 180° C. to completely dissolve the solids and to evaporate substantially all methanol carried over from Line 19.

The saturated solution from the First Dissolver 100 is then fed continuously to First Cooling Crystallizer 101 through Line 2 to generate TPA salt crystals at 30 to 50° C. The slurry containing TPA salt crystals exits First Cooling Crystallizer 101 through Line 3 to Filter I 102 where the crude crystal cake is removed and fed to Second Dissolver 103 through Line 4. In Second Dissolver 103, the cake is re-dissolved in clean NMP recycled through Line 35 from the solvent recovery system. Again, the temperature in Second Dissolver 103 is kept at 160 to 180° C. to completely dissolve the TPA salt crystals. The saturated solution from Second Dissolver 103 is continuously fed through Line 5 to Second Flash Crystallizer 104 where the temperature is maintained at a minimum of 60° C. to prevent the formation of TPA salt crystals. The degree of temperature reduction in the crystallizer is controlled by the amount of NMP flashed from the crystallizer through pressure reduction. The flashed NMP is recycled to the First Dissolver 100 through Line 36.

The slurry from Second Crystallizer 104 is fed to Filter II 105 through Line 6 where the purified TPA solid cake is recovered and sent to Cake Wash 106, while the mother liquor is recycled to First Dissolver 100 through Line 7. In Cake Wash unit 106, the bulk residual NMP in the cake is removed by counter-current washing with water and the washed cake is fed through Line 10 to a Soaker 107 to remove the final trace of NMP in the TPA solids by soaking with water at temperatures between 160 to 280° C. The NMP-free cake is filtered in Filter III 108 and dried in Dryer I 109 to yield the final TPA product.

The mother liquor from Filter I 102 is transferred through Line 15 to Precipitator 112. In doing so, it passes through Oxidizer 111, which is useful in the practice of a related invention disclosed and claimed in U.S. application Ser. No. 09/098, 060, entitled "Method to Reduce Carboxybenzaldehyde Isomers in Terephthalic Acid or Isophthalic Acid," owned by the assignee of the present application, whose disclosure is incorporated herein by reference for all purposes. Methanol is added to the precipitator through Line 16 to cause the complete precipitation (or crystallization) of TPA and a small amount of precipitation of IPA from the mother liquor. The slurry from Precipitator 112 is fed to Filter IV 113 through Line 18 to remove the major portion of the mother liquor from the slurry before it is recycled to First Dissolver 100 through Line 19.

The mother liquor from Filter IV 113 is sent to Evaporator 114 to remove NMP and methanol by evaporation through heat as well as vacuum, so that the concentrated mother liquor becomes a saturated solution of IPA, which is fed to First IPA Crystallizer 115 to crystallize IPA at a temperature between 30 to 50° C. by cooling or flashing. The vaporized NMP and methanol from Evaporator 114 is fed to Distillation Column 110 to yield NMP from the bottom and methanol from the top of the column. The methanol stream is recycled to Precipitator 112 through Line 16, while the NMP stream is fed to Second Dissolver 103 through Line 35. The slurry from First IPA Crystallizer I 15 is transferred to Filter V I 16 to produce crude IPA cake and the mother liquor. The mother liquor is sent to Precipitator 112 through Line 17, but a portion of Stream 17 is purged through Line 37 to prevent the accumulation of the impurities and color bodies.

The cake from Filter V 116 is then transferred through Line 25 to IPA Dissolver 1 17 where the crude IPA cake is dissolved by methanol at a suitable temperature and pressure. The saturated IPA solution is filtered in Filter VI 118 to remove the trace insolubles for purging through Line 28. The solid-free solution is fed through Line 29 to Second IPA Crystallizer 119 to yield IPA crystals by flashing methanol from the crystallizer through pressure reduction. The slurry from Second IPA Crystallizer 119 is transferred through Line 30 to Filter VII 120 to recover and wash the purified IPA crystals for final drying in Dryer II 121 to yield the final IPA product, while the mother liquor from Filter VII 120 is recycled the Evaporator 114 through Line 31.

Figure 2:
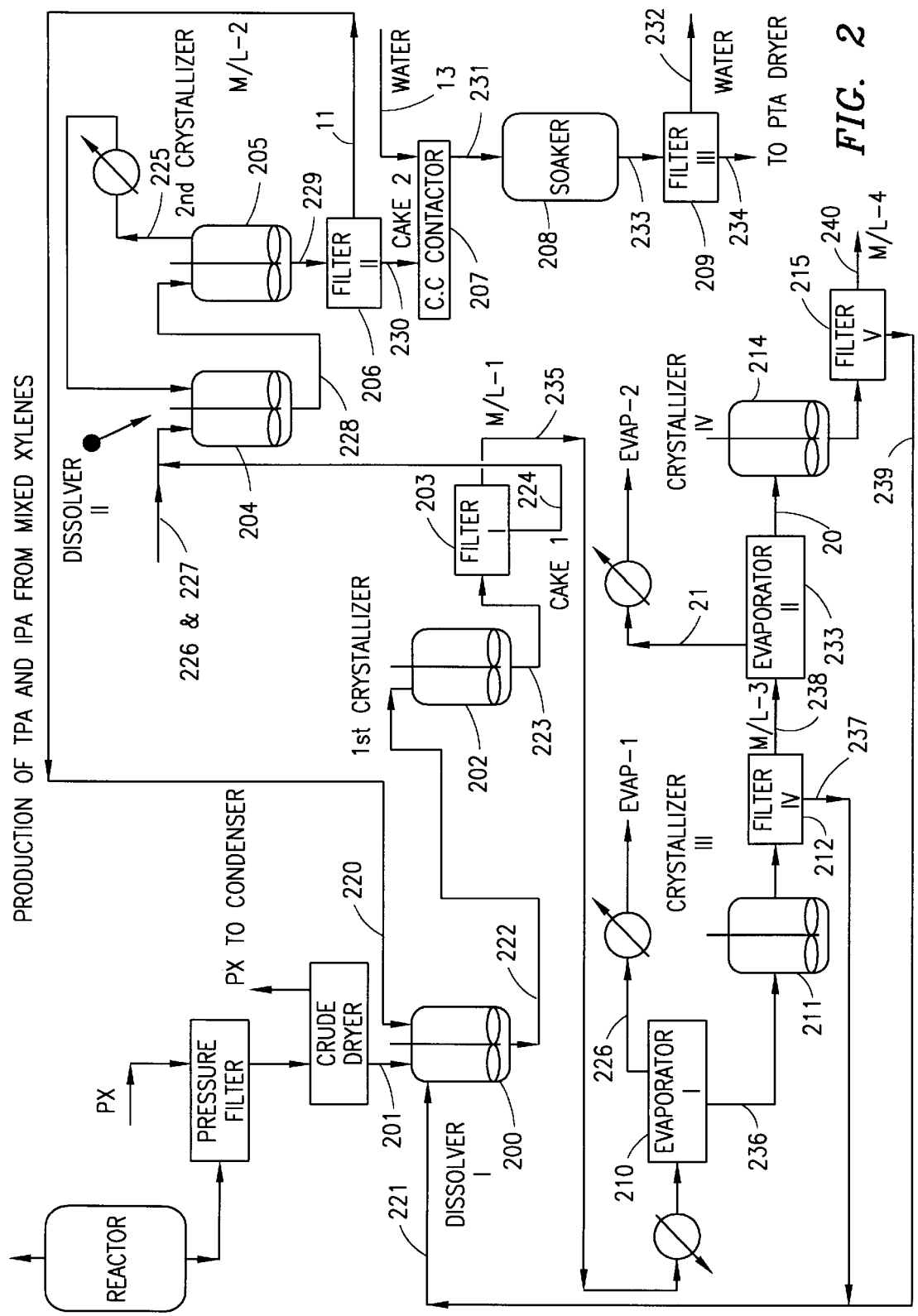
FIG. 2 is a diagrammatic flow chart for a plant for practicing another preferred embodiment of the invention for producing TPA only.

Another preferred embodiment of this invention for producing purified TPA only is illustrated in FIG. 2. The crude TPA (containing roughly 90 to 99% TPA and 1 to 10% IPA ) is fed to Dissolver I 200 through Line 201 to mix with the mother liquor M/L-2 from Filter II 206 (recycled through Line 220) and the recycled cake from Filter V 215 (recycled through Line 221). The temperature in the dissolver is maintained at 140 to 200° C. to dissolve substantially all the solids. The saturated solution is then fed through Line 222 to the First Crystallizer 202 where the temperature is reduced to 30 to 60° C. by cooling or solvent evaporation (with pressure reduction) to allow the TPA crystals to grow.

The slurry from First Crystallizer 202 is transferred continuously or batchwise through Line 223 to Filter I 203 to recover the solid cake. Washing the lean or saturated NMP is required at Filter I 203 to displace the mother liquor from the cake before it is transferred through Line 224 to Dissolver II 204, where the cake is mixed with the flashed NMP from Line 225 and evaporated NMP from Lines 226 and 227. Again, the temperature in Dissolver II 204 is maintained at 140 to 200° C. to dissolve substantially all the solids. The saturated solution is fed through Line 228 to Second Crystallizer 205 where the temperature is reduced to 30 to 60° C. by cooling or solvent evaporation (with pressure reduction) to allow the purified TPA crystals to grow.

Again, the slurry from Second Crystallizer 205 is fed through Line 229 to Filter II 206 to recover the cake, which is then transferred through Line 230 to a Counter-current Contactor 207 to be washed with water to remove the bulk of free NMP from the cake. The water-washed solids are sent through Line 231 to Soaker 208 to remove the trace amount of trapped NMP from the purified TPA solids by partial or total dissolving of the solids in Soaker 208 at a temperature of 150 to 280° C. The NMP-free solids are sent through Line 233 to Filter III 209 where the water is removed through Line 232 and the TPA cake is sent through Line 234 to be dried in a dryer to yield the final purified TPA product.

The mother liquor M/L-1 from Filter I 203 is sent through Line 235 to Evaporator I 210 to remove a substantial amount of NMP. The concentrated solution is transferred through Line 236 to Crystallizer III 211 to cause low-purity TPA crystals to grow. The crystals are then recovered from Filter IV 212 and recycled to Dissolver I 200 through Line 237. The mother liquor M/L-3 from Filter IV 212 is transferred via Line 238 to Evaporator II 213, then Crystallizer IV 214 and Filter V 215 to recover the residual low-purity TPA for recycling to Dissolver I 200 via Line 239. The final mother liquor M/L-4 from Filter V 215 containing mainly IPA, NMP and a minor amount of TPA passes through Line 240 and is to be treated for further NMP recovery by mixing with water before disposal.

What is claimed is:

1. A method for purifying crude terephthalic acid (TPA) from a liquid dispersion produced from the oxidation of mixed xylenes comprising:

(a) dissolving the crude TPA in a selective crystallization solvent at a temperature of from about 50° C. to about 250° C. to form a solution;

(b) crystallizing purified acid from said solution by reducing the temperature and/or pressure thereof;

(c) separating said crystallized purified TPA from said solution;

(d) redissolving said separated purified TPA in a selective crystallization solvent to form a second solution;

(e) crystallizing second stage purified TPA from said second solution by reducing the temperature and pressure sufficient to flash evaporate solvent from said TPA of said second solution but without cooling said solution below 50° C.;

(f) separating said second stage purified TPA from said second solution;

(g) washing said separated second stage purified TPA with water;

(h) soaking said washed separated second stage purified TPA with water at a temperature between about 150° C. and about 300° C.;

(i) filtering and drying said water soaked second stage purified TPA;

(j) adding an anti-solvent to said filtered solution in (c) to cause the precipitation of substantially all the TPA; and (k) separating said precipitated TPA from said solution in (j) and combining said precipitated TPA with said original crude TPA for processing in (a);

(l) evaporating the solvents from said filtered TPA-free solution in (k) to cause the crystallization of IPA at a temperature from about 5° C. and about 100° C.;

(m) separating said crystallized crude IPA from said solution in (1);

(n) redissolving crude IPA in a selective crystallization solvent at a temperature from about 500° C. to 250° C. to form a second solution;

(o) crystallizing purified IPA from said second solution in (n) by reducing the temperature and pressure sufficient to flash evaporate solvent from said IPA of said second solution but without cooling said solution below about 50° C.; and (p) separating and drying said second stage purified IPA from said second solution.

2. A method in accordance with claim 1 in which said dispersion contains at least 0 to 20% isophthalic acid (IPA), and minor amounts of 4-carboxyaldehyde (4-CBA), 3-carboxyaldehyde (3-CBA) and impurities selected from unreacted starting materials, solvents, products of side reactions and/or other undesired materials.

3. A method in accordance with claim 1 wherein said selective crystallization solvent for TPA purification is selected from the group consisting of N-methyl pyrrolidone, (NNV), N,N-dimethyl acetamide, N,N-dimethyl formamide, N-formyl piperidine, -alkyl-2-pyrrolidone, N-mercaptoalkyl-2-pyrrolidone, N-alkyl-2-thiopyrrolidone, N-hydroxyalkyl-2-pyrrolidone, the morpholines, the carbitols, $C_1$ to $C_{12}$ alcohols, the ethers, the amines, the amides, and the esters, and mixtures thereof.

4. A method in accordance with claim 3 wherein said selective crystallization solvent for TPA purification is N-methyl pyrrolidone or N,N-dimethyl acetamide.

5. A method in accordance with claim 4 wherein said selective crystallization solvent for TPA purification is N-methyl pyrrolidone.

6. A method in accordance with claim 1 wherein said anti-solvent for TPA precipitation from TPA/IPA solution is selected from the group consisting of methanol, water, methyl ethyl ketone, acetone, $C_1$ to $C_{12}$, alcohols, the carbitols, the esters, the ethers, $C_1$ to $C_{12}$ carboxylic acids, water, and mixtures thereof.

7. A method in accordance with claim 6 wherein said anti-solvent for TPA precipitation from TPA/IPA solution is methanol or water.

8. A method in accordance with claim 7 wherein said anti-solvent for TPA precipitation from TPA/IPA solution is methanol.

9. A method in accordance with claim 1 wherein said selective crystallization solvent for re-crystallization of IPA is selected from the group of methanol, water, methyl ethyl ketone, acetone, $C_1$ to $C_{12}$, alcohols, the carbitols, the esters, ethers, $C_1$ to $C_2$, carboxylic acids, water, and mixtures thereof.

10. A method in accordance with claim 9 wherein said selective crystallization solvent for re-crystallizing purified IPA is methanol or water.

11. A method in accordance with claim 1 wherein the said anti-solvent is at the antisolvent/solution ratio of 0.1 to 10 to cause the precipitation of TPA.

12. A method in accordance with claim 11 wherein the said anti-solvent/solution ratio is preferably in the range of 0.5 to 3.

13. A method for purifying crude terephthalic acid (TPA) from a liquid dispersion produced from the oxidation of mixed xylenes comprising:
(a) dissolving the crude TPA in a selective crystallization solvent at a temperature of from about 50° C. to about 250° C. to form a solution;
(b) crystallizing purified acid from said solution by reducing the temperature and/or pressure thereof;
(c) separating said crystallized purified TPA from said solution;
(d) redissolving said separated purified TPA in a selective crystallization solvent to form a second solution;
(e) crystallizing second stage purified TPA from said second solution by reducing the temperature and pressure sufficient to flash evaporate solvent from said TPA of said second solution but without cooling said solution below 50° C.;
(f) separating said second stage purified TPA from said second solution;
(g) washing said separated second stage purified TPA with water;
(h) soaking said washed separated second stage purified TPA with water at a temperature between about 150° C. and about 300° C.;
(i) filtering and drying said water soaked second stage purified TPA;
(j) concentrating said filtered solution in (c) by evaporation and cooling the concentrated solution to cause the crystallization of TPA and minor portion of IPA;
(k) separating said precipitated TPA and minor portion of IPA from said solution in (j) and recycling said solid mixture for processing in (a);
(l) concentrating said filtered solution in (k) by second evaporation and cooling the concentrated solution to cause further crystallization of TPA and minor portion of IPA;
(m) separating said crystallized TPA and minor portion of IPA from said solution in (l) and recycling solid mixture for processing in (a); and
n) transferring said filtered solution in (m) to waste treatment facility or to further processing.

14. A method in accordance with claim 13 in which said dispersion contains at least 0 to 20% isophthalic acid (IPA), and minor amounts of 4-carboxyaldehyde (4-CBA), 3-carboxyaldehyde (3-CBA) and impurities selected from unreacted starting materials, solvents, products of side reactions and/or other undesired materials.

15. A method in accordance with claim 13 wherein said selective crystallization solvent for TPA purification is selected from the group consisting of N-methyl pyrrolidone (NMP), N,N-dimethyl acetamide, N,N-dimethyl formamide, N-formyl piperidine, N-alkyl-2-pyrrolidone, N-mercaptoalkyl-2-pyrrolidone, N-alkyl-2-thiopyrrolidone, N-hydroxyalkyl-2-pyrrolidone, the morpholines, the carbitols, $C_1$ to $C_{12}$ alcohols, the ethers, the amines, the amides, and the esters, and mixtures thereof.

16. A method in accordance with claim 15 wherein said selective crystallization solvent for TPA purification is N-methyl pyrrolidone or N,N-dimethyl acetamide.

17. A method in accordance with claim 16 wherein said selective crystallization solvent for TPA purification is N-methyl pyrrolidone.

18. A method for purifying crude terephthalic acid (TPA) and isophthalic acid (IPA) from a liquid dispersion produced from the oxidation of mixed xylenes comprising: (a) dissolving the crude TPA in a selective crystallization solvent at a temperature of from about 50° C. to about 250° C. to form a solution;
(b) crystallizing purified acid from said solution by reducing the temperature and/or pressure thereof, and separating said crystallized purified TPA from said solution;
(c) repeating said dissolution and crystallizing of said TPA, if necessary, to obtain a purified TPA of desired purity;
(d) adding an anti-solvent to the said solution from which said crystallized purified TPA was separated to cause the precipitation of substantially all the TPA remaining in said solution;
(e) separating said precipitated TPA;
(f) evaporating the solvents from the solution obtained by adding an anti-solvent and removing the precipitated TPA to cause crystallization of IPA, and purifying and recovering purified IPA thereby.

19. A method in accordance with claim 18 and further comprising dissolving and crystallizing said purified IPA to obtain IPA of desired purity.

20. A method in accordance with claim 18 in which said dispersion contains at least 0 to 20% isophthalic acid (IPA), and minor amounts of 4-carboxyaldehyde (4-CBA), 3-carboxyaldehyde (3-CBA) and impurities selected from unreacted starting materials, solvents, products of side reactions and/or other undesired materials.

21. A method in accordance with claim 18 wherein said selective crystallization solvent for TPA purification is selected from the group consisting of N-methyl pyrrolidone, (NMP), N,N-dimethyl acetamide, N,N-dimethyl formamide, N-formyl piperidine, N-alkyl-2-pyrrolidone, N-mercaptoalkyl-2-pyrrolidone, N-alkyl-2-thiopyrrolidone, N-hydroxyalkyl-2-pyrrolidone, the morpholines, the carbitols, $C_1$ to $C_{12}$ alcohols, the ethers, the amines, the amides, and the esters, and mixtures thereof.

22. A method in accordance with claim 18 said anti-solvent for TPA precipitation from TPA/IPA solution is selected from the group consisting of methanol, water, methyl ethyl ketone, acetone, $C_1$, to $C_{12}$, alcohols, the carbitols, the esters, the ethers, $C_1$, to $C_{12}$ carboxylic acids, water, and mixtures thereof.

* * * * *

UNITED STATES PATENT AND TRADEMARK OFFICE
CERTIFICATE OF CORRECTION

PATENT NO.    : 6,054,610
DATED         : April 25, 2000
INVENTOR(S)   : Lee et al.

It is certified that error appears in the above-identified patent and that said Letters Patent is hereby corrected as shown below:

Column 3,
Line 31, replace "formarnide" with -- formamide --

Column 8,
Line 61, replace "I 15" with -- 115 --
Line 62, replace " I 16" with -- 116 --
Line 67, replace "1 17" with -- 117 --

Colum 10,
Line 33, replace "500°C." with -- 50°C. --
Line 52, replace "(NNV)" with -- (NMP) --

Column 11,
Line 63, replace "n)" with -- (n) --

Column 12,
Line 60, insert -- wherein -- after "claim 18"
Line 63, replace "$C_1$," with -- $C_1$ --
Line 63, replace "$C_{12}$," with -- $C_{12}$ --
Line 64, replace "$C_1$," with -- $C_1$ --

Signed and Sealed this

Twenty-sixth Day of February, 2002

Attest:

*Attesting Officer*

JAMES E. ROGAN
*Director of the United States Patent and Trademark Office*